United States Patent [19]

Orem et al.

[11] 3,936,451

[45] Feb. 3, 1976

[54] PROCESS FOR PRODUCING SALTS OF HEXAMETHYLENETETRAMINE

[75] Inventors: Henry Philip Orem; David R. Hart, both of Birmingham; Jerry E. Hill, Springville, all of Ala.

[73] Assignee: United States Pipe and Foundry Company, Birmingham, Ala.

[22] Filed: Aug. 27, 1974

[21] Appl. No.: 500,845

[52] U.S. Cl. .............................. 260/248.5; 424/249
[51] Int. Cl.² ........................................ C07D 251/04
[58] Field of Search ................................ 260/248.5

[56] References Cited
UNITED STATES PATENTS

| | | |
|---|---|---|
| 3,372,091 | 3/1968 | Harnett et al. ............... 260/248.5 X |
| 3,597,428 | 8/1971 | Hechenbleikner ............... 260/248.5 |
| 3,638,703 | 2/1972 | Endter et al. ..................... 260/248.5 |
| 3,772,285 | 11/1973 | Winans et al. .................... 260/248.5 |

*Primary Examiner*—John M. Ford
*Attorney, Agent, or Firm*—James W. Grace

[57] ABSTRACT

A process for producing a salt of hexamethylenetetramine (hexa), such as the tolulene sulfonic acid (TSA) - hexa salt, by mixing an acid with hexamethylenetetramine and only enough solvent such as water to promote the reaction. Excess heat liberated by the reaction is controlled by cooling the mixing chamber and drying is accomplished in a heated or ambient atmosphere except for hygroscopic salts which are easily dried in a vacuum or may be dried in a very dry atmosphere.

4 Claims, No Drawings

PROCESS FOR PRODUCING SALTS OF HEXAMETHYLENETETRAMINE

BACKGROUND OF THE INVENTION

This invention relates to the field of preparing salts of hexamethylenetetramine. The preparation of certain salts of hexamethylenetetramine has long been known. These comprise both inorganic salts such as chloride, sulfate, phosphate, chlorate and organic salts such as formate, methanesulfonate, benzenesulfonate, p-toluenesulfonate, naphthalenesulfonate and many others. These salts are useful as chemical intermediates and as medicinals. Some have been employed as an ingredient for formation of a resin which is incorporated in rubber to increase the adhesion of the rubber to automobile tire cord. Hexa-salts are also used as curing agents for chemical resins. The known processes for preparation of such salts require that both the hexamethylenetetramine and the acid be in a relatively dilute aqueous solution or suspension or that the solvent be an aromatic hydrocarbon. Several processes for producing salts of hexamethylenetetramine are described in U.S. Pat. Nos. 3,597,428 and 3,772,285. These processes may be satisfactory for producing small amounts of salts of hexamethylenetetramine but require objectionable steps when considered for large quantity production. For instance, U.S. Pat. No. 3,597,428 reveals a process wherein the salt is formed in a water solution and is subsequently spray dried at a high temperature (150°C to 317°C). This very rapid drying prevents the salt from hydrolyzing; however, spray drying such solutions requires expensive equipment and utilizes considerable heat to evaporate the large amounts of water contained in the solution. Water content of the preferred solution revealed in U.S. Pat. No. 3,597,428 (50% acid solution, 58% hexamethylenetetramine mixed 1 to 1) can be calculated to be a minimum of 45%. A process for producing aromatic sulfonic acid salts of hexamethylenetetramine is revealed in U.S. Pat. No. 3,772,285. However, producing such salts by this method requires the difficult steps of handling and recovering a relatively expensive solvent, part of which is lost. There is further difficulty in removing the solvent from the solid salt as there is the possibility of fire or explosion, as well as pollution of the air with aromatic fumes. Further, in a commercial process there would be a build-up in any recycled liquids requiring an eventual disposal problem. Also, the process is restricted to aromatic sulfonic acid salts.

SUMMARY OF THE INVENTION

In the production of salts of hexamethylenetetramine one problem has always been paramount. This problem, well recognized by the prior art, is the prevention of hydrolysis prior to and during drying of the salt. The applicant has discovered that if only a small amount of a solvent such as water is introduced, along with the hexamethylenetetramine and acid, drying may be accomplished at relatively low temperatures, and since very little solvent is made available hydrolysis is virtually eliminated. It is believed that the small amount of solvent is used to promote the reaction or as a catalyst in the reaction of the acid and the hexamethylenetetramine and as the salt is formed it is precipitated so rapidly from the very temporary solution that it does not remain in the liquid phase long enough to undergo significant decomposition.

The present invention is a novel process for preparing salts of hexamethylenetetramine using well-known, relatively inexpensive mixing and drying equipment requiring a low input of energy and reactants when compared with known methods. While the process requires a solvent as an aid to carrying out the reaction between the acid and the base, the amount of solvent required is held to a minimum, thus minimizing the amount of heat required to dry the resulting salt, all of which minimizes the tendency of the salt to hydrolyze. Mixing is accomplished by charging the hexamethylenetetramine into either a dough mixer, pug mill, pony mixer, paddle mixer, ball mill, ribbon mixer or the like and then adding the acid and solvent at a relatively constant rate. The rate will vary for preparing various salts and in some cases it may be desirable to add the solvent and acid as a single ingredient. It may also be found advantageous for producing certain salts to add all ingredients at a constant rate. There are also certain cases where it may be advantageous to use hydrated organic acids such as benzenesulfonic acid monohydrate, p-toluenesulfonic acid monohydrate, m-xylenesulfonic acid dihydrate. It is also apparent that the present invention encompasses continuous formation of hexamethylenetetramine salts by metering the ingredients into an appropriate mixer. Examples of acids which can be used to prepare the salts by applicants' method include those listed in the prior art such as sulfuric acid, hydrochloric, perchloric acid, phosphoric acid, chromic acid, dimethyl phosphoric acid, phenyl phosphonic acid, methane phosphonic acid, o-xylene-4-sulfonic acid, benzene sulfonic acid, monophenyl phosphoric acid, methane sulfonic acid, ethane sulfonic acid, p-toluene sulfonic acid, o-toluene sulfonic acid, m-toluene sulfonic acid, trichloroacetic acid, a-naphthalene sulfonic acid, b-naphthalene sulfonic acid, methane diphosphonic acid, methane disulfonic acid, d-camphoric acid, 1-camphoric acid, o-phenol sulfonic acid, p-phenol sulfonic acid, boric acid, salicylic acid, quinic acid, 3-sulfosalicylic acid, o-sulfobenzoicacid, acetylaminosalicylic acid, 1,5naphtahalene disulfonic acid, diisopropyl naphtalene sulfonic acid, dibutyl naphthalene sulfonic acid, dl-mandelic acid, d-mandelic acid, benzoic acid, caproic acid, isobutyric acid, formic acid, phthalic stearic acid, oleic acid, linoleic acid, lauric acid, palmitic acid, sebacic acid, ricinoleic acid, oxalic acid, abietic acid, phenylacetic acid, malonic acid, succinic acid, glutaric acid, adipic acid, valeric acid, tartaric acid, phenyl propionic acid, cinnamic acid, b-oxyhydrocinnamic acid, arsenous acid, citric acid, tannic acid and malic acid.

An object of the invention is to produce salts of hexamethylenetetramine using readily available, relatively inexpensive equipment.

Another object of the invention is to produce salts of hexamethylenetetramine utilizing a minimum of energy.

Yet another object of the invention is to produce salts of hexamethylenetetramine in a very efficient manner where the recovery of the dried salt is a high percentage of input ingredients.

It is also an object of the invention to carry out the process without a polluting effluent.

DESCRIPTION OF THE PREFERRED EMBODIMENT

Applicants' preferred embodiment may be better understood from the following examples wherein all amounts are parts by weight.

EXAMPLE 1

A sigma-blade, double-arm dough mixer (such mixers being well known to those familiar with the art) was charged with 900 parts of hexamethylenetetramine and 1204.1 parts of a crystalline substance containing 84.5% toluenesulfonic acid, 2.68% sulfuric acid and the remainder water. These ingredients were added simultaneously and were mixed for two and one-fourth hours then poured from the mixer into a pan which was placed in an enclosure (pan dryer) and air at 65° C was passed through the dryer. During mixing the temperature of the ingredients increased from 23° C to 48° C and at first was a soft paste-like substance and then hard and crystalline. The dry product consisted of 1935.5 parts of Hexamethylenetetramoniumtoluenesulfonate. It should be noted that the process yield was about 99.2 percent of all material, excluding the water, charged into the mixer. Also, the water was less than eight per cent of the material charged.

The small amount of heat liberated may be heat of reaction and/or heat of crystallization of the newly formed salt. This heat, if sufficient, could cause more rapid decomposition and thus, in some cases, it becomes necessary to cool the mixing chamber by water jacket or spray cooling the outside of the chamber or by circulating air through the mixer or by other well-known means. This extraction of heat, direct or through the mixer wall or shell, does not alter the steps of the process and only becomes necessary where the quantity of heat liberated is sufficient to be detrimental to the process. Applicants' experience with drying salts of hexamethylenetetramine formed as described in the present invention show that as the materials initially react and are in the pasty soft stage they are much more susceptible to decomposition at a given temperature than they are as they become hard and crystalline in texture. In consideration of this characteristic, it is suggested that drying temperatures can be increased up to 110° C as the drying cycle progresses. However, initial drying temperatures should be held below 70° C. Duration and method of drying varies with the particular hexa-salt. While drying was accomplished to an essentially constant weight in the examples herein, commercial production would not necessarily require such stringent measures. In most cases a user specification will require that moisture content be below a certain specified minimum. Further examples of salts of hexamethylenetetramine produced by applicants' novel process are described below wherein all amounts are parts by weight.

EXAMPLE 2

A sigma-blade, double-arm dough mixer was charged with 424 parts of hexamethylenetetramine and while mixing 293.6 parts of a solution of 89% methanesulfonic acid and 11% water was added at a constant rate for a period of 19 minutes. The combined ingredients were mixed an additional 30 minutes; then poured into a tray and allowed to dry at room temperature (about 27° C). During mixing the temperature increased from 30° C to 43° C. After the product dried, there were 673.2 parts, representing a yield of 98.2 percent.

EXAMPLE 3

A sigma-blade, double-arm dough mixer was charged with 840 parts of hexamethylenetetramine. The mixer was started and 1079.7 parts of a solution of 90% phenolsulfonic acid and 10% water was added at a constant rate during a period of one hour. The combined ingredients were mixed for an additional 45 minutes. The temperature of the mix rose from 30° C to 55° C. The mixer was cooled to prevent the temperature from rising above 55° C. The material was poured from the mixer into pans and placed in a vacuum oven at 40° C until dry. There were 1694 parts of the dried product which was slightly yellow in color representing a 93.5 percent yield.

EXAMPLE 4

A sigma-blade, double-arm dough mixer was charged with 848 parts of hexamethylenetetramine. The mixer was started and 1080 parts of benzenesulfonic acid monohydrate (11% water) was added at a constant rate for one-half hour. The materials were then mixed for two and one-half hours. The temperature rose from 36° C to 42° C. The resulting salt became a hard crushable solid and was discharged from the mixer into pans and dried in a vacuum oven at 40° C. After drying, there remained 1752 parts of the product representing a 96.8 percent yield.

EXAMPLE 5

A sigma-blade, double-arm dough mixer was charged with 848 parts of hexamethylenetetramine. The mixer was started and 1369.5 parts of m-xylenesulfonic acid dihydrate (16.2% water) was added over a period of one-half hour.

The materials were mixed for one hour and ten minutes during which time the temperature rose from 30° C to 48° C. The material was discharged into pans and dried at room temperature (about 27° C). After drying, there remained 1896.4 parts of the product representing 95.0% yield.

EXAMPLE 6

A sigma-blade, double-arm dough mixer was charged with 420 parts of hexamethylenetetramine. The mixer was started and 348.9 parts of m-benzenedisulfonic acid monohydrate (7% water) was added at a constant rate over a period of one-half hour and the material mixed for an additional 45 minutes. The temperature rose from 34° C to 50° C. The material was discharged from the mixer into pans and dried in a vacuum oven at 30° C. After drying, 712.1 parts of the material remained representing 95.6 percent yield.

EXAMPLE 7

A sigma-blade, double-arm dough mixer was charged with 848 parts of hexamethylenetetramine. The mixer was started and 770.8 parts of oxalic acid dihydrate (28.6% water) was added over a period of one hour. The ingredients were mixed for five hours and their temperature rose from 31° C to 46° C. The material was discharged from the mixer into pans and was dried in an oven at 55° C. The dried material consisted of 1398 parts representing 100.0 percent yield.

EXAMPLE 8

A sigma-blade, double-arm dough mixer was charged with 848 parts of hexamethylenetetramine. The mixer was started and 819.6 parts of malic acid containing only 0.37% water was added at a constant rate over a period of 30 minutes. The materials were mixed an additional 45 minutes and the temperature rose from 31° C to 70° C. The material was discharged from the mixer into pans and dried in a vacuum oven at 30° C. The dried material consisted of 1406 parts representing 84.5 percent yield.

EXAMPLE 9

A sigma-blade, double-arm dough mixer was charged with 700 parts of hexamethylenetetramine. The mixer was started and 612.5 parts of a solution of 80% sulfuric acid and 20% water was added at a constant rate over a period of two hours. The ingredients were mixed an additional one-half hour and the temperatures rose from 28° C to 45° C. The material was discharged from the mixer and dried in an oven at 50° C. The dried material consisted of 1190 parts representing 100.0 percent yield.

EXAMPLE 10

A sigma-blade, double-arm dough mixer was charged with 700 parts of hexamethylenetetramine. The mixer was started and 493.5 parts of a solution of 37% hydrochloric acid, 63% water, was added at a constant rate over a period of one and one-half hours. The ingredients were mixed an additional forty-five minutes and the temperature rose from 27° C to 41° C. The material was discharged from the mixer and dried in an oven at 70° C. The dried material consisted of 844.4 parts representing 95.7 percent yield.

EXAMPLE 11

A sigma-blade, double-arm dough mixer was charged with 1045.0 parts of beta-resorcylic acid, 209.0 parts of water and 1000.3 parts of hexamethylenetetramine. The mixer was started and mixing was continued for three and one-half hours and the temperature rose from 19° C to 37° C. The product was discharged and dried for 17 hours at 65° C to give a light tan colored material. The beta-resorcylic acid had a moisture content of 0.32% giving a total solids charged of 2011.9 parts and a recovery of 1990.5 parts of product giving a yield of 98.9 percent recovery of total material charged excepting the water.

EXAMPLE 12

A sigma-blade, double-arm dough mixer was charged with 1147.0 parts of hexamethylenetetramine, 278.9 parts water, and 929.2 parts of benzoic acid. The mixer was started and stirred for seven hours with the temperature of the material rising from 22° C to 29° C. The product was discharged and dried for seventeen hours at 70° C to a slightly yellow product weighing 2034 parts. This represents a recovery of 98.0 percent of the material charged excepting the water.

EXAMPLE 13

A sigma-blade, double-arm dough mixer was charged with 820 parts of hexamethylenetetramine and while the mixer was running, a slurry containing 989 parts of 96.3% p-toluenesulfonic acid and 200 parts of isopropyl alcohol was added over a period of eleven minutes. Mixing was continued for another 54 minutes until the temperature had risen from 32° C to 62° C. Mixing was discontinued and the product was allowed to cool to 43° C in the mixer over a period of one hour. The product was discharged from the dough mixer and was then dried for 44 hours at 55° C in an air oven. The product yield was 1746 parts, representing a yield of 98.5 percent based on the materials charged to the dough mixer, excluding isopropyl alcohol.

EXAMPLE 14

A sigma-blade, double-arm dough mixer was charged with 1000 parts of p-toluenesulfonic acid, monohydrate, CP grade (50ppm $H_2SO_4$) and 750 parts hexamethylenetetramine. The mixer was run for 170 minutes during which time the reaction mixture became quite fluid and the temperature rose from 27° C to 51° C. The mixer was shut off in order to allow the reaction mixture to crystallize. After 60 minutes the product of the reaction was crystalline and the temperature had risen to 65° C. The product was discharged from the dough mixer, and dried at 75° C for 17 hours in an air dryer. 1602 parts of the product were obtained, a recovery of 96.8 percent of the material charged to the dough mixer, excluding the water of hydration in the toluenesulfonic acid.

EXAMPLE 15

A sigma-blade, double-arm dough mixer was charged with 700 parts of hexamethylenetetramine and 580 parts of maleic acid. The dry ingredients were mixed for 10 minutes and then 120 parts of N-N dimethylformamide were added uniformly over an 8-minute period during which time the temperature rose from 27° C to 30° C. The mixing was continued for another 90 minutes during which the temperature rose from 30° C to 52° C and the appearance of the mixture passed from a damp crystal through a doughy substance and then to a dry appearing solid. The product was broken up and dried for 24 hours at 60° C and a pressure of 20mm of mercury. A yield of 1269 parts were obtained representing a recovery of 99.2 percent of the starting materials, excluding N-N dimethylformamide.

EXAMPLE 16

A sigma-blade, double-arm dough mixer was charged with 700 parts of hexamethylenetetramine and 580 parts maleic acid. The mixer was started and the solids were mixed for 10 minutes. Sixty parts of water were added over an 8-minute period while mixing. Mixing was continued for another 112 minutes during which time the mixture passed through a dough-like state and then to a hard solid. The temperature of the charge rose from 29° C to 44° C during the operation. The product was discharged from the mixer and dried in a vacuum dryer for 115 hours at 45° C and a pressure of 20mm of mercury. A yield of 1271 parts were obtained representing a recovery of 99.3 percent of the charged materials, excluding the water.

EXAMPLE 17

A sigma-blade, double-arm dough mixer was charged with 980 parts of hexamethylenetetramine. The mixer was started, and 358 parts of 90% formic acid (10% water) were added at a uniform rate over an 18-minute period. The temperature during the addition rose from 30° C to 48° C. Mixing was continued for another 60 minutes, and the product was discharged and dried at 45° C and 20mm Hg for 70 hours. A yield of 121 parts was obtained, representing a recovery of 92.9 percent of the starting materials, excluding the water content of the formic acid.

The salt formed in each of the examples is listed below:

| EXAMPLE NO. | NAME OF ACID | NAME OF SALT |
|---|---|---|
| 1 | p-Toluenesulfonic Acid | Hexamethylenetetrammonium p-Toluenesulfonate |
| 2 | Methanesulfonic Acid | Hexamethylenetetrammonium Methanesulfonate |
| 3 | Phenolsulfonic Acid | Hexamethylenetetrammonium Phenolsulfonate |
| 4 | Benzenesulfonic Acid | Hexamethylenetetrammonium Benzenesulfonate |
| 5 | m-Xylenesulfonic Acid | Hexamethylenetetrammonium m-Xylenesulfonate |
| 6 | m-Benzenedisulfonic Acid | Hexamethylenetetrammonium m-Benzenedisulfonate |
| 7 | Oxalic Acid | Hexamethylenetetrammonium Oxalate |
| 8 | Malic Acid | Hexamethylenetetrammonium Malate |
| 9 | Sulfuric Acid | Hexamethylenetetrammonium Bisulfate |
| 10 | Hydrochloric Acid | Hexamethylenetetrammonium Chloride |
| 11 | beta-Resorcylic Acid | Hexamethylenetetrammonium beta-Resorcylate |
| 12 | Benzoic Acid | Hexamethylenetetrammonium Benzoate |
| 13 | p-Toluenesulfonic Acid | Hexamethylenetetrammonium p-Toluenesulfonate |
| 14 | p-Toluenesulfonic Acid | Hexamethylenetetrammonium p-Toluenesulfonate |
| 15 | Maleic Acid | Hexamethylenetetrammonium Maleate |
| 16 | Maleic Acid | Hexamethylenetetrammonium Maleate |
| 17 | Formic Acid | Hexamethylenetetrammonium Formate |

From the above examples, it can be readily seen that salts of hexamethylenetetramine can be produced when the acid and base are mixed with samll amounts of solvent and that virtually no hydrolysis takes place even though temperatures become elevated substantially.

While the maximum or minimum amounts of solvent that may be utilized successfully in applicants' process will vary depending on what acid is being used, it is evident from Example 8 that the minimum approaches zero and from Example 10 that as much as 26 percent of the total material charged may be solvent. Drying of the salts may be accomplished in a medium other than air, such as an inert gas or mixture of gases that would not affect the salt being dried. However, for the best results, the medium should be relatively dry and the temperature of the medium maintained below that which would cause decomposition of the salt. Also, drying may be accomplished in various devices such as ovens, rotary dryers or by heating the mixer during the drying cycle.

The herein described embodiments and examples of the present invention are not intended to limit its scope; it is to be understood that modifications and variations may be resorted to without departing from the spirit and scope of the invention as claimed herein below.

We claim:

1. A method of preparing a salt of hexamethylenetetramine comprising:
   thoroughly mixing hexamethylenetetramine, water, and an acid wherein the acid is selected from the group consisting of p-Toluenesulfonic Acid, Methanesulfonic Acid, Phenolsulfonic Acid, Benzenesulfonic Acid, m-Xylenesulfonic Acid, m-Benzenedisulfonic Acid, Oxalic Acid, Malic Acid, Sulfuric Acid, Hydrochloric Acid, beta-Resorcylic Acid, Benzoic Acid, Maleic Acid, and Formic Acid, in which mixture the amount of water is less than 26 percent by weight,
   controlling the temperature of the mixture during the mixing stage below that which would cause decomposition; and
   drying the mixture at a temperature less than that which would cause decomposition.

2. A method of preparing a salt of hexamethylenetetramine as recited in claim 1 in which the amount of water is from about 0.18 percent of said mixture to about 26 percent of said mixture.

3. A method of preparing a salt of hexamethylenetetramine as recited in claim 1 which said temperature of said mixture is kept from rising above 70° C. during said mixing stage.

4. A method of preparing a salt of hexamethylenetetramine as recited in claim 1 in which said drying temperature of said mixture after said mixing stage is kept from rising above 110° C.

* * * * *